United States Patent
Johnsen (10) Patent No.: US 7,642,534 B2
(45) Date of Patent: Jan. 5, 2010

(54) MULTILEAF COLLIMATOR FOR ELECTRON RADIOTHERAPY

(75) Inventor: Stanley W. Johnsen, Palo Alto, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 261 days.

(21) Appl. No.: 11/823,468

(22) Filed: Jun. 26, 2007

(65) Prior Publication Data
US 2009/0001295 A1    Jan. 1, 2009

(51) Int. Cl.
*G21K 1/02* (2006.01)
(52) U.S. Cl. .............. 250/505.1; 250/515.1; 250/492.1; 378/147; 378/150
(58) Field of Classification Search .............. 250/505.1, 250/515.1, 492.1; 378/147, 150
See application file for complete search history.

(56) References Cited

U.S. PATENT DOCUMENTS

| | | | |
|---|---|---|---|
| 4,794,629 A * | 12/1988 | Pastyr et al. | 378/152 |
| 4,868,844 A * | 9/1989 | Nunan | 378/152 |
| 5,012,506 A * | 4/1991 | Span et al. | 378/152 |
| 5,889,834 A * | 3/1999 | Vilsmeier et al. | 378/147 |
| 6,730,924 B1 * | 5/2004 | Pastyr et al. | 250/505.1 |
| 6,813,337 B2 * | 11/2004 | Svatos et al. | 378/65 |
| 6,819,743 B2 * | 11/2004 | Kato et al. | 378/147 |
| 7,397,902 B2 * | 7/2008 | Seeber et al. | 378/152 |
| 7,507,975 B2 * | 3/2009 | Mohr | 250/492.1 |
| 2001/0043669 A1 * | 11/2001 | Ein-Gal | 378/152 |
| 2004/0184578 A1 * | 9/2004 | Nakano | 378/65 |
| 2005/0063516 A1 * | 3/2005 | Kato et al. | 378/152 |
| 2005/0185766 A1 * | 8/2005 | Tsujita | 378/150 |
| 2006/0067480 A1 * | 3/2006 | Juschka et al. | 378/150 |
| 2007/0127624 A1 * | 6/2007 | Seeber et al. | 378/147 |

FOREIGN PATENT DOCUMENTS

JP    2007037828 A    *    2/2007

* cited by examiner

*Primary Examiner*—David A Vanore
*Assistant Examiner*—Michael J Logie
(74) *Attorney, Agent, or Firm*—Lumen Patent Firm (57) ABSTRACT

A flexible multi-leaf collimator for electron radiotherapy is provided, where the leaves are not a single rigid component, but are configured in a manner that curves away from the patient to provide greater clearance. The invention includes a plurality of flexible assemblies, at least one guide supporting the assemblies, and a plurality of assembly drivers. The driver engages the assembly and moves the assembly along the guide. The assembly has an extended state and a retracted state relative to the guide, such that when in the extended state the assembly is held in the aperture plane and when in the retracted state the assembly conforms along the guide. When in the extended state the assemblies are disposed as a treatment aperture.

9 Claims, 6 Drawing Sheets

United States Patent US 7,642,534 B2

MULTILEAF COLLIMATOR FOR ELECTRON RADIOTHERAPY

FIELD OF THE INVENTION

The invention relates generally to collimating treatment beams for radiotherapy. More particularly, the invention relates to a flexible aperture assembly that enables collimating a treatment beam in close proximity to a patient to limit radiation dispersion in a treatment area.

BACKGROUND

When beams of high energy x-rays or electrons are used for radiotherapy, it is important to direct the beams to a tumor within the patient, while restricting the beams from striking healthy tissue outside the tumor region. Tumors commonly have irregular shapes and it is necessary to shape the beam cross-section to the corresponding irregular shape. It is common for the treatment plan to prescribe the beam to be directed at the tumor from a number of different angles, where the beam profile is unique for each corresponding angle.

Currently, radiotherapy accelerators producing therapeutic electron beams utilize "applicators", also known as "cones", are attached to the therapy machine to provide a final collimation aperture along the beam path before the tumor is exposed. The applicator defines the final beam cross-section profile and it is desirable to place the applicator as close to the patient as possible to limit exposure to healthy tissue. Because the tumor has a unique shape for each prescribed exposure angle, a unique collimating aperture is required for each corresponding angle. It is common to have multiple apertures fabricated for treating a single tumor, where alloys with low melting temperatures are typically cast into the required irregular shapes. The cast apertures can be interchanged with the radiotherapy device to provide a beam that conforms to the shape of the area to be irradiated. These unique apertures are expensive and time consuming to fabricate.

In an attempt to alleviate the need to fabricate a unique aperture for each exposure, multi-leaf collimators (MLC) have been implemented as a way to shape the beam cross-section. These devices include a set of flat, thin leaves made from a high-density material, such as tungsten, where each leaf in moved transversely in and out of the radiation field to selectively attenuate portions of the beam to create a unique beam cross-section. The shape of the beam can be altered dynamically during the therapy session using motorized controls connected to each leaf. By dynamically attenuating select portions of the beam, intensity-modulated radiotherapy (IMRT) has been made possible, where by moving the leaves during beam exposure, the beam can be delivered in a manner such that the spatial fluence of the irradiation is not constant over the irradiated area. IMRT can also be accomplished by making multiple irradiations, each with a different field shape, the sum of which creates a field of non-uniform intensity. The leaves must be thick enough to highly attenuate the beam. For example, when using x-ray beams, at least a 6 cm thickness of tungsten is required.

X-ray MLC's are typically mounted as far from the patient as practicable to ensure maximum clearance between the radiotherapy machine and the patient. In accordance with some accelerators, the MLC has been used to replace the standard field-shaping jaws of the accelerator. The shape of the portion of the leaf that defines the edge of the field is designed for minimum penumbra to create the sharpest edge of the beam as possible between the irradiated and protected areas.

In electron radiotherapy, fabricated electron applicators are typically used, where the applicators are customized for each patient to define each unique final beam aperture. This process is very time consuming and expensive. The custom aperture must be installed by hand for each treatment field. If two or more fields are used for a therapy session, the aperture must be changed for each field. Further, the aperture must be redesigned to accommodate changes in the tumor size during the course of treatment. The beneficial practice of IMRT delivery cannot be used with these fixed apertures.

It is desirable to be able to use multi-leaf collimators for electron irradiation as well as for x-ray irradiation. Currently, MLC's that are designed for x-rays are not suitable to this end. To produce a desired penumbra, a collimator for electron beams must be close to the patient surface, typically within 5 cm. Conversely, the usual location of an x-ray MLC is far from the patient, which makes creating desirable beam characteristics unfeasible. It is possible to move the patient closer, but the penumbra achievable still cannot match that which is attained with an electron applicator.

Attempts to create the final aperture of an electron applicator using a form of MLC have been reported. In these efforts, the final aperture of the applicator has been constructed of a bank of leaves that can be moved to a variable position relative to the beam, similar to an x-ray MLC. The leaves do not have to be as thick as those for x-ray MLC's, where it requires only approximately 1 cm of brass to stop 20 MeV electrons compared to the 6 cm of more of tungsten required for an effective x-ray MLC.

Figure 1:
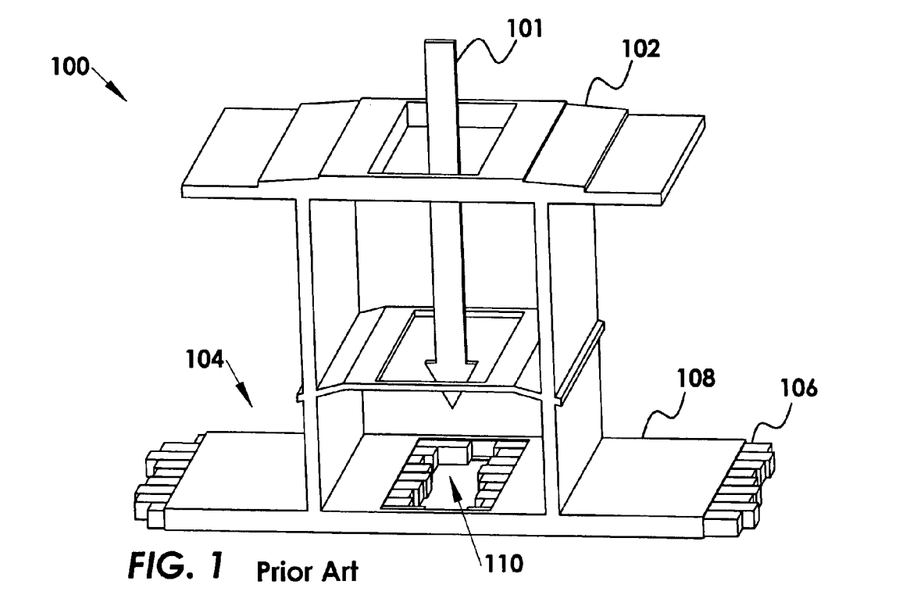
FIG. 1 shows a perspective view of a prior art applicator and multi-leaf collimator assembly for use with an electron beam.

FIG. 1 shows a perspective view of a prior art applicator and multi-leaf collimator assembly 100 for use with electron beams 101, where shown is an applicator 102 and a multi-leaf collimator 104 having two opposing sets of movable leaves 106 configured to move parallel with one another in a collimator housing 108 disposed as a treatment aperture 110. As shown, the leaves 108 are positioned manually however motorized leaves are also known in the art.

Figure 2:
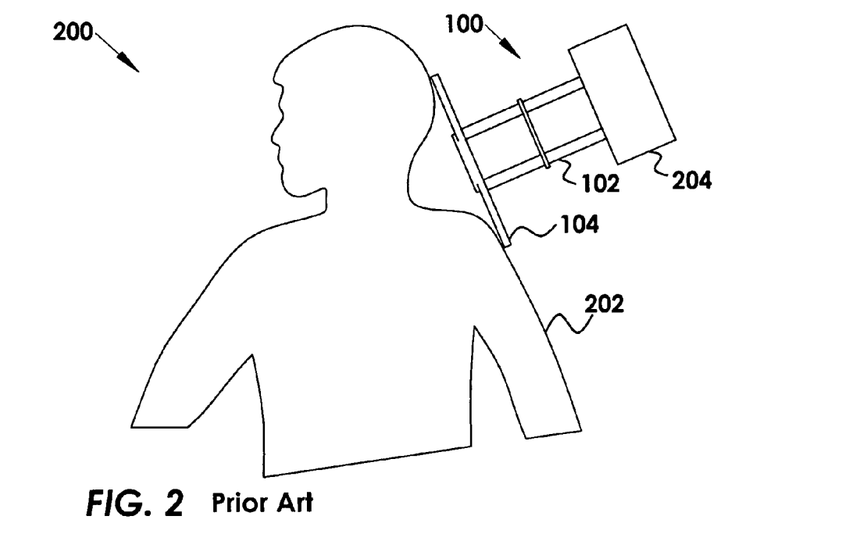
FIG. 2 shows a planar view of a treatment configuration with a patient positioned close to a prior art applicator and multi-leaf collimator assembly attached to an accelerator.

FIG. 2 is a planar view of a treatment configuration 200, where a patient 202 is positioned close to the prior art multi-leaf collimator assembly 100 attached to an accelerator 204. Here, the large extensions of the MLC 104 to each side of the treatment field prevent the applicator 102 from being positioned close to irregular surfaces on the patient 202, such as near the head and neck. This results in the final aperture 110 being further away from the patient 202 than desired, and prevents optimization of the penumbra.

Accordingly, there is a need to minimize the lateral extention of the electron applicator near the patient and minimize clearance issues to overcome the current shortcomings in the art.

SUMMARY OF THE INVENTION

According to the current invention, a flexible multi-leaf collimator is provided that includes a plurality of flexible assemblies, at least one guide supporting the assemblies, and a plurality of assembly drivers. The driver engages the assembly and moves it along the guide. The assembly has an extended state and a retracted state relative to the guide, such that when in the extended state, the assembly is held in an aperture plane and when in the retracted state, the assembly conforms along the guide.

In one aspect of the invention, the assembly is a flexible assembly that includes at least two collimator segments, where the segment has a first side and a second side. The first side of one the segment interfaces the second side of an adjacent segment. The flexible assembly further includes a flexible conveyor, where the conveyor can be a flexible top strap attached to the top of each the segment and is disposed along the guide. The first segment in the series is an assembly collimation end and a last segment in the series is an assembly actuation end.

In another aspect of the invention, the conveyor can further include a flexible opposing strap, where the assembly collimation end is connected to a first end of the opposing strap and the assembly actuation end is connected to a second end of the opposing strap.

According to a further aspect of the invention, the conveyor can be a plurality of pivotable linkages to provide a pivotable connection between the segments. Here, a first end of the segment top surface is pivotably connected to a second end of an adjacent segment top surface.

In another aspect of the invention, the conveyor can include an interlock strap having interlock nodes disposed to engage a node socket on a bottom surface of the segment. When the assembly is in the extended state the node is engaged in the socket and when the assembly is in the retracted state the node is disengaged from the socket.

In yet another aspect of the invention, the segment has a first side and a second side, where the first side has a first engagement feature and the second side has a second engagement feature such that the first engagement feature engages the second engagement feature.

In another aspect of the invention, the assembly can be a flexible assembly made from a graduated-length stack of at least two flexible straps disposed along the guide.

According to another aspect of the invention, the guide is a curved guide having an upper guide surface and a lower guide surface, where the upper surface has a smaller radius of curvature than a radius of curvature of the lower surface. In this aspect, the guide further has a guide collimation end and a guide actuation end, where the guide collimation end is disposed about perpendicular to a radiation beam path and the guide actuation end is disposed about parallel to the beam path.

In a further aspect of the invention, the driver can be a computer-controlled actuator, where the actuator engages an actuation end of the assembly and moves the assembly along the guide.

Some key advantages are the leaves of the flexible MLC being curved away from the patient surface to allow better access to the patient. The invention resolves the problem of having an array of rigid leaves occupying a plane near the patient surface, and can replace the standard final aperture in an electron applicator. A further advantage is the ability of the flexible leaves to be positioned dynamically and remotely, enabling faster patient treatments and the use of IMRT techniques with electron radiotherapy.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides leaves with an MLC for electron radiotherapy where the leaves are not a single rigid component, but are configured in a manner that curves away from the patient to provide greater clearance. According to the current invention, a flexible multi-leaf collimator is provided that includes a plurality of flexible assemblies, at least one guide supporting the assembly, and a plurality of assembly drivers. The driver engages the assembly and moves the assembly along the guide. The assembly has an extended state and a retracted state relative to the guide, such that when in the extended state the assembly is held in the aperture plane and when in the retracted state the assembly conforms along the guide.

Figure 3:
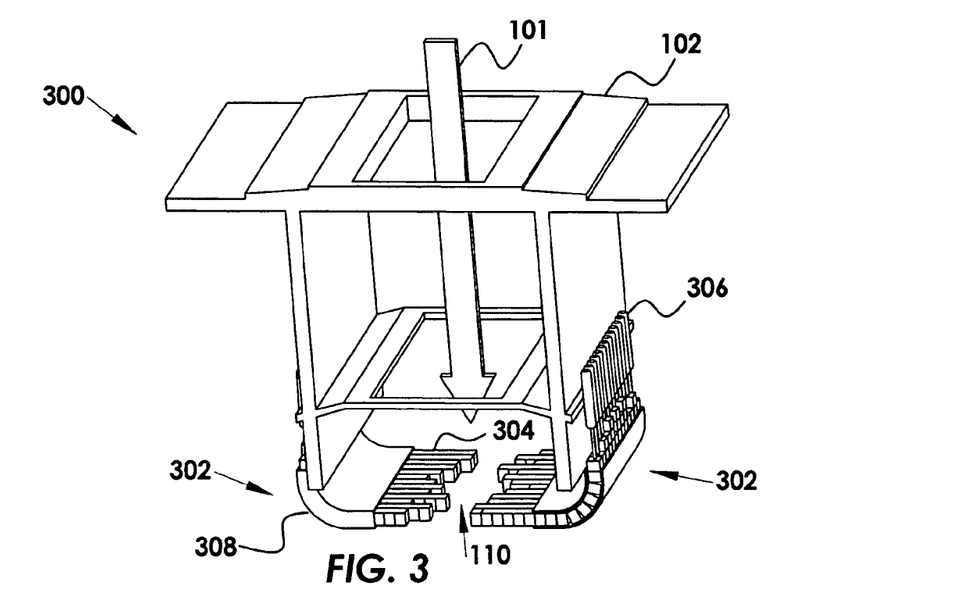
FIG. 3 shows a perspective view of an applicator and flexible multi-leaf collimator assembly for use with an electron beam according to the current invention.

FIG. 3 shows a perspective view of an applicator and flexible multi-leaf collimator assembly 300 for use with an electron beam 101. As shown, an applicator 102 has an opposing pair of flexible multi-leaf collimators 302 attached to the end of the applicator 102. The flexible leaves 304 are driven by drivers 306, such as computer controlled positioning motors, to move within a guide 308 and extend horizontally out of the guide 308 to form an aperture 110. Accordingly, the aperture 110 can be dynamic or static during treatment. The flexible leaves 304 are able to bend away from the patient according to the profile of the guide 308. In the drawing, one guide 308 is shown as a partial-cutaway to illustrate the flexible leaves 304.

Figure 4:
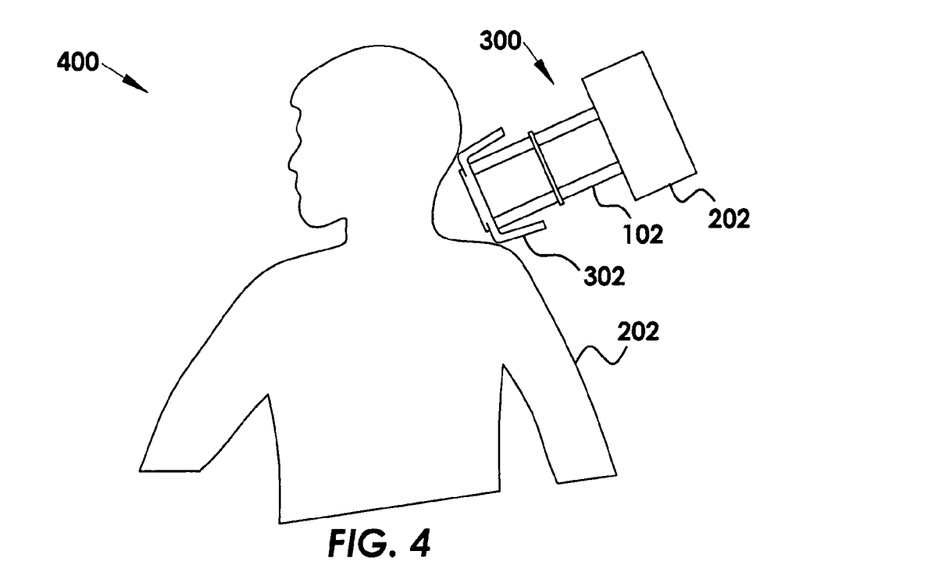
FIG. 4 shows a planar view of a treatment configuration with a patient positioned close to an applicator and flexible multi-leaf collimator assembly attached to an accelerator according to the current invention.

FIG. 4 shows a planar view of a flexible MLC treatment configuration 400 with a patient 202 positioned close to the applicator and flexible MLC-applicator assembly 300 attached to an accelerator 202. As shown, the flexible MLC 302 curves away from the patient 202 to provide greater clearance to the curvatures of the patient 202.

FIGS. 5a-5b show perspective views of the flexible multi-leaf collimator 302 according to one embodiment of the invention. Shown is a flexible MLC 302 having multiple flexible leaves 304. The flexible leaves 304 include multiple collimator segments 500 attached to a flexible conveyor 502. The segments 500 are thick enough to provide the desired attenuation of the electron beam 101. The conveyor 502 and attached segments 500 move along a guide 308 when actuated by the driver 306. The guides 308 are shown as curved and illustrated in partial perspective cutaway views to show the aspects of the flexible leaves 304 and how they translate within the guides 308. The drivers 306 can be operated using computer commands (not shown).

Figure 5:
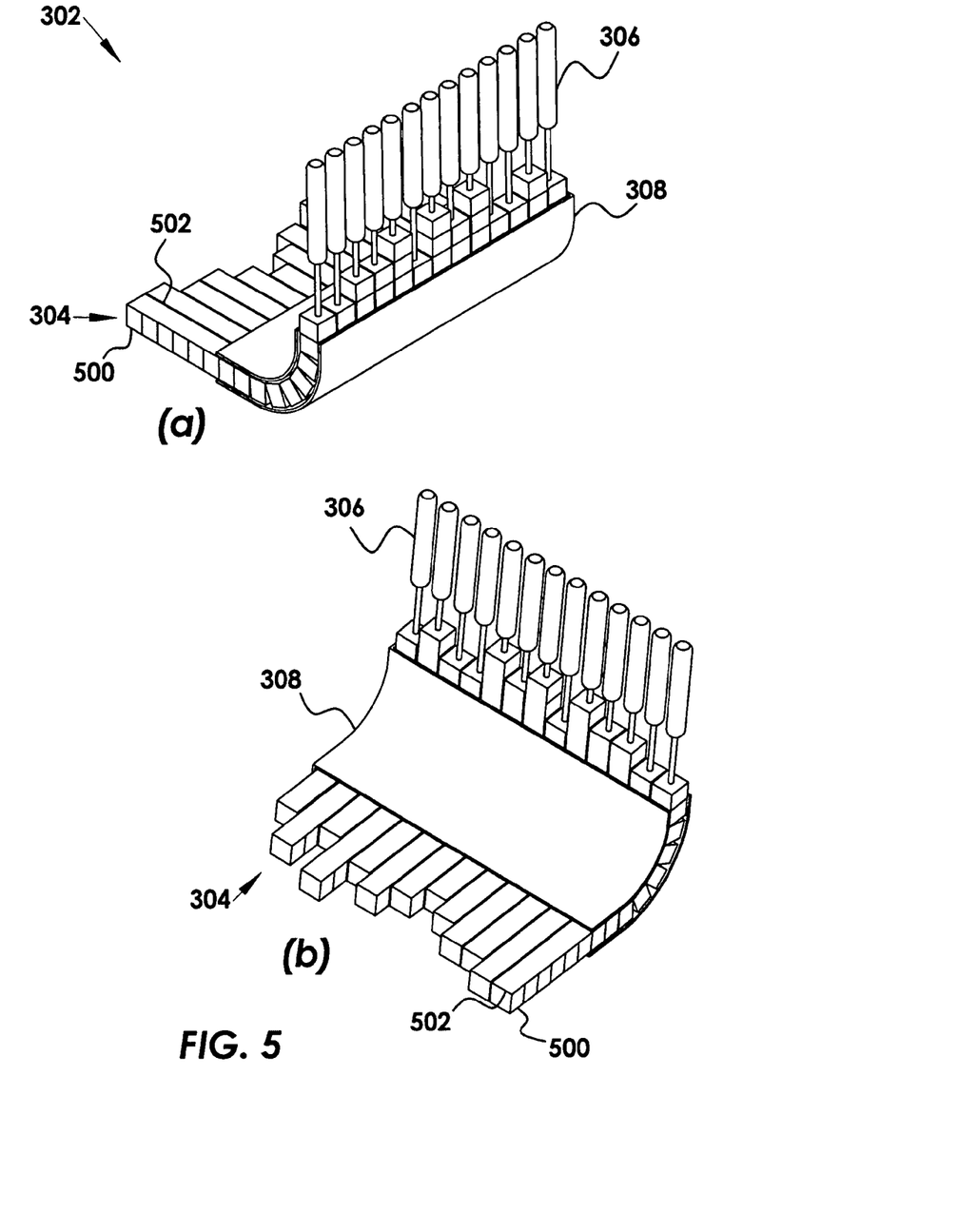
FIGS. 5a-5b show perspective views of a flexible multi-leaf collimator according to one embodiment of the current invention.
Figure 6:
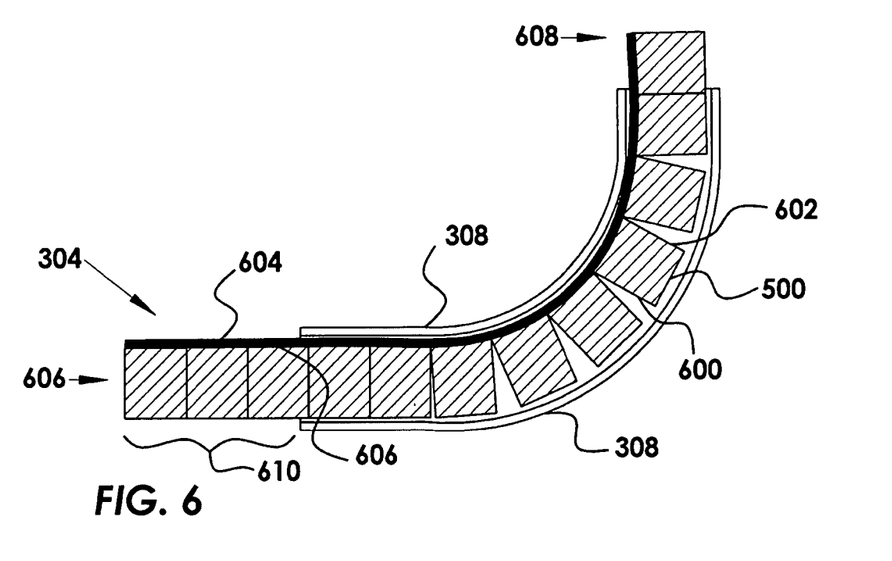
FIG. 6 shows one embodiment of a flexible assembly of collimator elements in a guide according to the current invention.

FIG. 6 shows one embodiment of the flexible leaf 304 of collimator elements 500 in a guide 308 according to the current invention. The flexible leaves 304 include at least two collimator segments 500, where the segment 500 has a first segment side 600 and a second segment side 602. Here, the first side 600 of one the segment 500 interfaces the second side 602 of an adjacent segment 500. The conveyor 502 of FIG. 5 is shown in FIG. 6 as a flexible top strap 604 attached to a topside 606 of each the segment 500, where the top strap 600 is disposed along the guide 308. In this embodiment, a first segment 606 in the series is the assembly collimation end 606 and a last segment 608 in the series is the assembly actuation end 608, where the collimation end 606 provides the desired penumbra, and the actuation end 608 is incorporated to the driver 306 (not shown). The adjacent segments 500 form a rigid assembly 610 as they extend from the guide 308.

Figure 7:
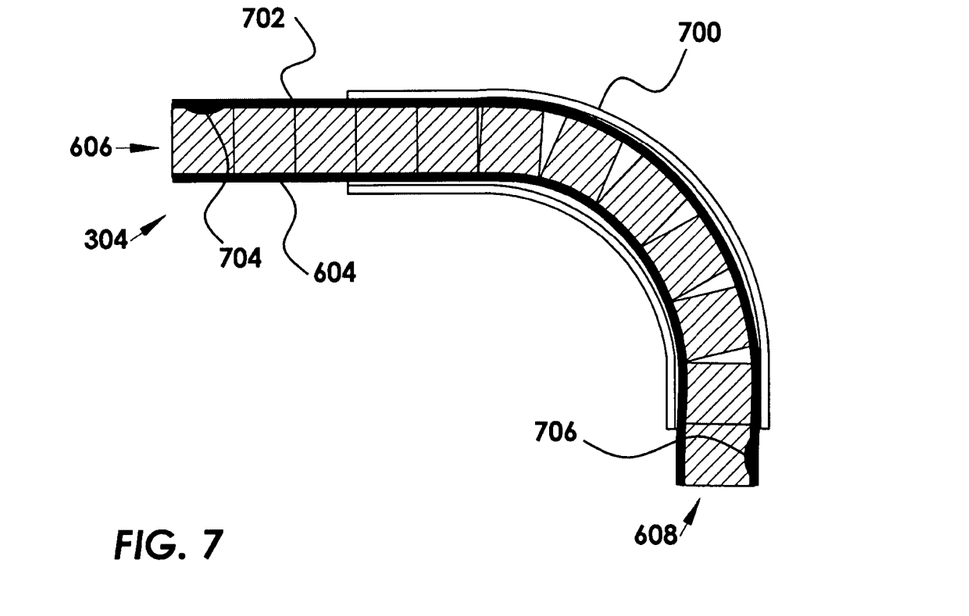
FIG. 7 shows one embodiment of a flexible assembly of collimator elements in an inverted guide according to the current invention.

FIG. 7 shows another embodiment of the flexible leaf 304 of collimator elements 500 oriented upside down, relative to the embodiment of FIG. 6, in an inverted guide 700. In this embodiment, the conveyor 502 of FIG. 5 includes the aspects of the flexible top strap 604 embodiment of FIG. 6, but inverted here, in addition to a flexible opposing strap 702, where the assembly collimation end 606 is connected to a opposing strap first end 704 and the assembly actuation end 608 is connected to a the opposing strap second end 706. The segments 500 between the collimation end 606 and actuation end 608 are not attached to the opposing strap 702. In this embodiment, the combination of straps (604, 702) serves to hold the segments 500 rigidly in place as they extend from the guide 308 to define the radiation field.

Figure 8:
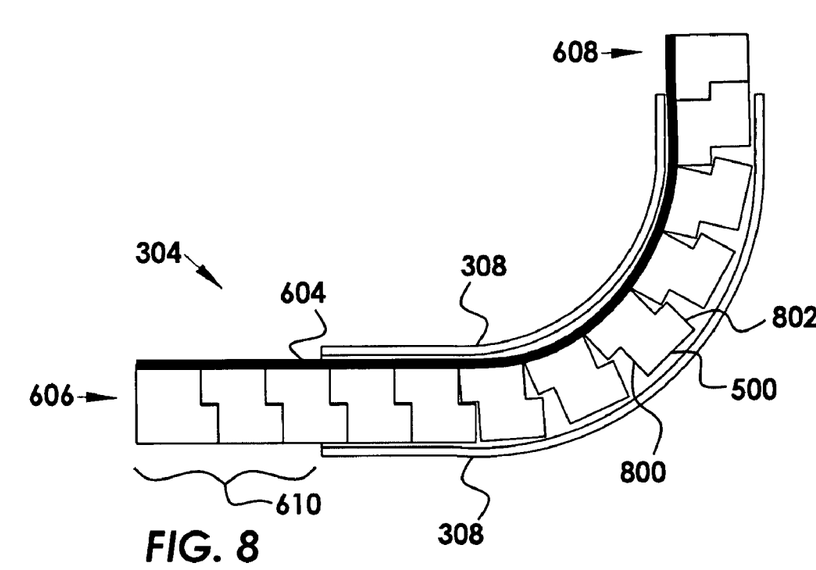
FIG. 8 shows one embodiment of a flexible assembly of collimator elements having interlock features between the elements according to the current invention.

FIG. 8 shows another embodiment of the invention, where the collimator elements 500 of the flexible assembly 304 of have interlock features between the elements 500 allowing them to join with each other when in an extended state. As shown, the elements 500 have a first engagement feature 800 on the first side and a second engagement feature 802 on the second side, where the first engagement feature 800 of one the segment 500 interfaces the second engagement feature 802 of an adjacent segment 500. In this example, the flexible top strap 604 is shown, however other conveyors may be used to provide similar results. In this embodiment, the engagement of the features (800, 802) on the adjacent segments 500 forms a rigid assembly 610 as they extend from the guide 308.

Figure 9:
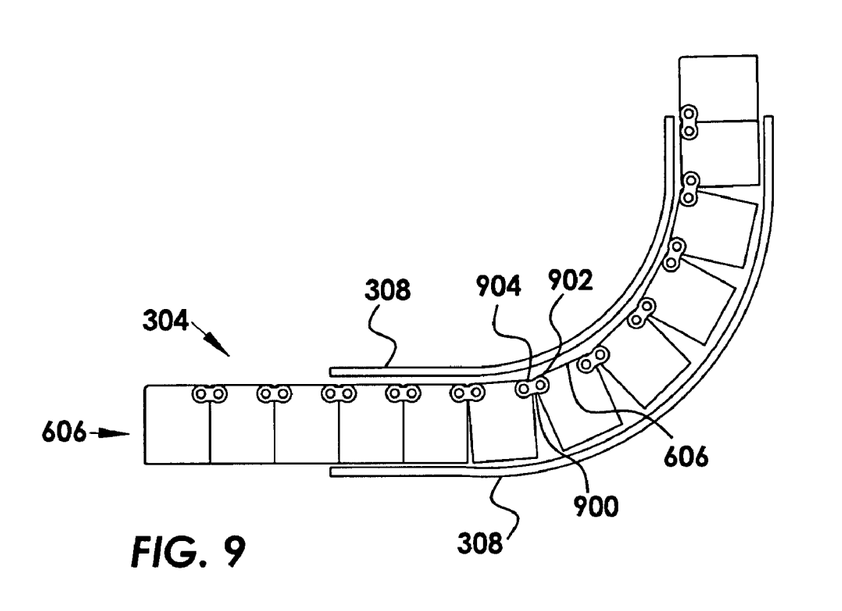
FIG. 9 shows one embodiment of a flexible assembly of collimator elements having pivotable interconnects between the elements according to the current invention.

FIG. 9 shows a further embodiment of the flexible leaves 304 of collimator elements 500 having pivotable interconnects 900 between the elements 500. Here, the conveyor 502 of FIG. 5, is shown as a plurality of pivotable linkages 900 that provide a pivotable connection between the segments 500, where a first end 902 of a segment top surface 606 is pivotably connected to a second end 904 of an adjacent segment top surface 606.

Figure 10:
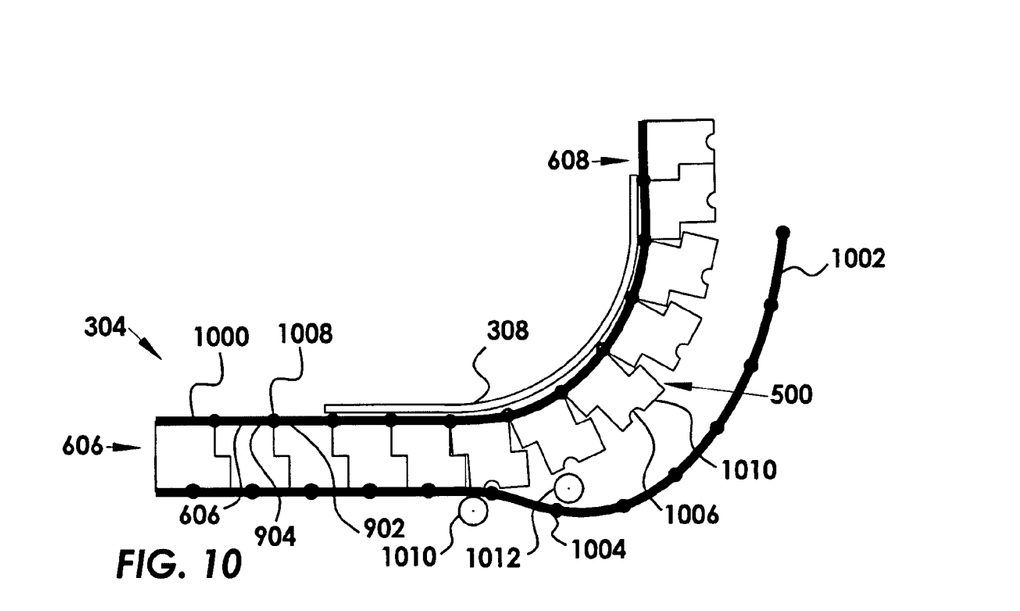
FIG. 10 shows one embodiment of a flexible assembly of collimator elements having a lower conveyor with nodes for fitting to element sockets according to the current invention.

FIG. 10 shows one embodiment of the flexible leaves 304 of collimator elements 500 having a pivotable-linkage top conveyor 1000 and a lower interlock conveyor 1002 with nodes 1004 for fitting to element sockets 1006. As shown, the pivotable-linkage top conveyor 1000 has of pivotable linkages 1008 to provide a pivotable connection between the segments 500, where a first end 902 of a segment top surface 606 is pivotably connected to a second end 904 of an adjacent segment top surface 606. The interlock conveyor 1002 has interlock nodes 1004 disposed to engage the node socket 1006 on a segment bottom surface 1010. When the assembly 304 is in the extended state the node 1004 is engaged in the socket 1006 and when the assembly is in the retracted state the node 1004 is disengaged from the socket 1006. The engagement of the interlock node 1004 to the node socket 1006 is facilitated by an engagement mechanism 1010 to hold the elements 500 as a rigid assembly as they extend from the guide 308, and disengagement of the node 1004 to the socket 1006 is facilitated by a disengagement mechanism 1012.

Figure 11:
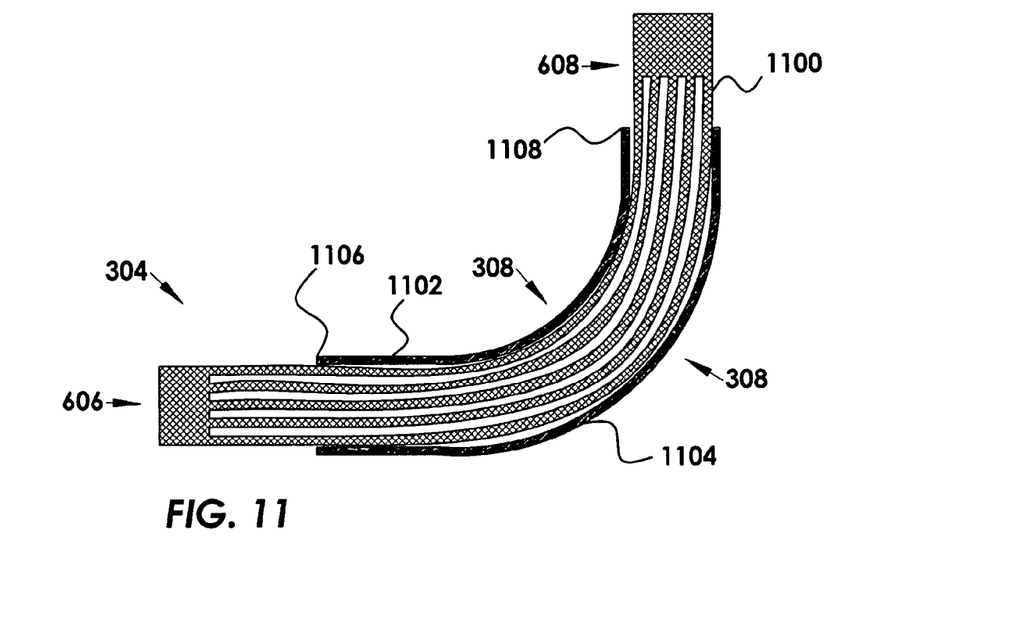
FIG. 11 shows one embodiment of a flexible assembly having a stack of graduated-length flexible elements in a guide according to the current invention.

FIG. 11 shows one embodiment of a flexible leaves 304 having a stack of graduated-length flexible elements 1100 fastened together at each end 606 and 608 in a guide 308 according to the current invention. Here, the guide 308 is curved having an upper guide surface 1102 and a lower guide surface 1104, where the upper surface 1102 has a smaller radius of curvature than a radius of curvature of the lower surface 1104. In this aspect, the guide 308 further has a guide collimation end 1106 and a guide actuation end 1108, where the guide collimation end 1106 is disposed about perpendicular to a radiation beam path (not shown) and the guide actuation end 1108 is disposed about parallel to the beam path (not shown). The combined thickness of the elements 1100 in the direction parallel to the radiation beam 101 (not shown) is sufficient to provide the desired attenuation of the beam 101 (not shown).

It should be evident from the above descriptions that many combinations of conveyors 502, guides 308, drivers 306 and elements 500 are possible without detracting from the spirit of the invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A flexible multi-leaf collimator comprising:
   a. at least one flexible leaf;
   b. at least one curved guide supporting said at least one flexible leaf; and
   c. at least one leaf driver, wherein said at least one leaf driver engages said at least one flexible leaf and moves said at least one flexible leaf along said at least one curved guide, wherein said at least one flexible leaf has an extended state and a retracted state relative to said at least one curved guide, wherein when in said extended state said at least one flexible leaf is held in an aperture plane and when in said retracted state said at least one flexible leaf conforms along said at least one curved guide.

2. The flexible collimator of claim 1, wherein said at least one flexible leaf comprises:
   a. at least two collimator segments, wherein said collimator segments comprise a first side and a second side, wherein said first side of one said collimator segment interfaces said second side of an adjacent said collimator segment; and
   b. a flexible conveyor, wherein said conveyor comprises a flexible top strap attached to a topside of said collimator segment, wherein a first said collimator segment in said series comprises a flexible leaf collimation end and a last said segment in said series comprises a flexible leaf actuation end, wherein said top strap is disposed along said curved guide.

3. The flexible collimator of claim 2, wherein said conveyor further comprises a flexible opposing strap, wherein said a flexible leaf collimation end is connected to a first end of said opposing strap and said a flexible leaf actuation end is connected to a second end of said opposing strap.

4. The flexible collimator of claim 2, wherein said conveyor comprises a plurality of pivotable linkages to provide a pivotable connection between said collimator segments, wherein a first end of a collimator segment top surface is pivotably connected to a second end of an adjacent collimator segment top surface.

5. The flexible collimator of claim 2, wherein said conveyor further comprises an interlock strap, wherein said interlock strap comprises interlock nodes disposed to engage a node socket on a bottom surface of said collimator segments, wherein when said assembly is in said extended state said node is engaged in said socket and when said assembly is in said retracted state said node is disengaged from said socket.

6. The flexible collimator of claim 2, wherein said segments comprise a first side and a second side wherein said first side comprises a first engagement feature and said second side comprises a second engagement feature, wherein said first engagement feature engages said second engagement feature.

7. The flexible collimator of claim 1, wherein said at least one flexible leaf is a flexible assembly comprising a graduated-length stack of at least two flexible straps disposed along said guide.

8. The flexible collimator of claim 1, wherein said curved guide comprising:
   a. an upper guide surface and a lower guide surface, wherein said upper surface has a smaller radius of curvature than a radius of curvature of said lower surface;
   b. a guide collimation end; and
   c. a guide actuation end, wherein said guide collimation end is disposed about perpendicular to a radiation beam path and said guide actuation end is disposed about parallel to said beam path.

9. The flexible collimator of claim 1, wherein said leaf driver comprises a computer controlled actuator wherein said actuator engages an actuation end of said flexible leaf and moves said flexible leaf along said guide.

* * * * *